(12) United States Patent
Vallance et al.

(10) Patent No.: US 6,916,115 B1
(45) Date of Patent: Jul. 12, 2005

(54) SYSTEM AND DEVICE FOR CHARACTERIZING SHAPE MEMORY ALLOY WIRES

(75) Inventors: Robert Ryan Vallance, South Riding, VA (US); Bruce L. Walcott, Lexington, KY (US); James E. Lumpp, Lexington, KY (US); Sumanth Chikkamaranahalli, Alexandria, VA (US); Osamah A. Rawashdeh, Lexington, KY (US); Eric Wolsing, Shoals, IN (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 10/792,974

(22) Filed: Mar. 4, 2004

Related U.S. Application Data

(60) Provisional application No. 60/451,802, filed on Mar. 4, 2003.

(51) Int. Cl.[7] .......................... G01N 25/00; G01N 3/14
(52) U.S. Cl. ................................ 374/55; 374/6; 73/760
(58) Field of Search ................................ 374/6, 45, 46, 374/49, 52, 55, 208, 43; 73/760

(56) References Cited

U.S. PATENT DOCUMENTS

| | | | |
|---|---|---|---|
| 3,079,790 A | | 3/1963 | MacDonnell |
| 3,774,440 A | | 11/1973 | Martinelli |
| 3,969,930 A | | 7/1976 | Prevorsek et al. |
| 4,056,973 A | | 11/1977 | Prevorsek et al. |
| 4,191,053 A | * | 3/1980 | Hart et al. ............... 374/112 |
| 4,562,743 A | | 1/1986 | Bonine |
| 4,579,006 A | | 4/1986 | Hosoda et al. |
| 4,599,905 A | | 7/1986 | Vogel et al. |
| 4,998,825 A | | 3/1991 | Hublikar et al. |
| 5,209,568 A | * | 5/1993 | Buffard et al. ............ 374/49 |
| 5,248,200 A | | 9/1993 | Walsh |
| 5,495,772 A | | 3/1996 | Dinzburg et al. |
| 5,563,390 A | * | 10/1996 | Demissy .................. 218/154 |
| 5,659,141 A | | 8/1997 | DeSpain |
| 6,008,992 A | * | 12/1999 | Kawakami .............. 361/726 |
| 6,290,037 B1 | * | 9/2001 | Williams et al. .......... 188/379 |
| 6,851,260 B2 | * | 2/2005 | Mernøe .................... 60/527 |

FOREIGN PATENT DOCUMENTS

| | | | | |
|---|---|---|---|---|
| JP | 60166766 | * | 8/1985 | ............ F03G/7/06 |
| JP | 2241989 | * | 9/1990 | ............ F03G/7/26 |

OTHER PUBLICATIONS

Dinalloy, Inc. Technical Characteristics of FLEXINOL actuator wires. Date unknown.

C. Liang et al. Design of shape memory alloy actuators. Journal of Mechanical Design. Jun. 1992. vol. 114. pp. 233–230.

C. Liang. et al. One–Dimensional Thermomechanical Constitutive Relations for Shape Memory Materials. Apr., 1990. J. of Intell. Mater. Syst. and Struct. vol. 1. pp. 207–234.

* cited by examiner

*Primary Examiner*—Gail Verbitsky
(74) *Attorney, Agent, or Firm*—King & Schickli, PLLC

(57) ABSTRACT

Instruments and methods for measuring a property of a shape memory alloy are provided. The instrument includes a base plate, a non-contact movable mass, a force gauge, an actuator, a biasing spring, a heater for heating the shape memory alloy, and a non-contact displacement detector. The biasing spring and the shape memory alloy are disposed whereby a force applied thereby is applied substantially through a center of stiffness of the movable mass. The displacement detector measures a displacement of the movable mass in a colinear direction with a direction of movement of the movable mass and with a direction of the force applied by the biasing spring and the shape memory alloy. The linear motion stage comprises a housing and at least one guide bar, and wherein a calculated axial expansion of the guide bar is substantially equal to a calculated axial expansion of the base plate.

33 Claims, 11 Drawing Sheets

SYSTEM AND DEVICE FOR CHARACTERIZING SHAPE MEMORY ALLOY WIRES

This application claims the benefit of U.S. Provisional Patent Application Ser. No. 60/451,802, filed Mar. 4, 2003.

TECHNICAL FIELD

The present invention relates to applications making use of shape memory alloy (SMA), and more specifically to methods and instruments for characterizing the properties of SMA subjected to repeated cycles of contraction and elongation.

BACKGROUND OF THE INVENTION

The term shape memory alloy (SMA) is applied to that group of metallic compounds that demonstrate the ability to return to some previously defined shape or size when subjected to appropriate thermal procedure. These materials can be plastically deformed at relatively low temperature, and upon exposure to higher temperature will return to their shape prior to deformation. The basic physics involved in the shape memory effect is a reversible martensitic transformation. Repeated heating and cooling of these alloys results in cyclic motion, which provides utility as thermal actuators. This feature may be used in robotic applications where repeated shape, geometry and positions are required.

Shape memory alloy actuators exist in a variety of forms such as ribbons, wires and thin films. The recovery force generated by a constrained shape memory element acts in the direction of the recoverable shape change and this can be used to perform work Bias spring actuators often use SMA wires that contract when heated above their transformation temperatures. During cooling, the wire relaxes and may be elongated, for example using a biasing spring.

One important application of SMA is in force actuators, wherein the SMA component is designed to exert force over a considerable range of motion, often for many cycles. Shape memory alloys have received increasing attention in recent years, especially in the development of innovative engineering systems such as micro-actuators. The use of SMA as actuators in robotic application attempts to take advantage of their large capacities in motion and force transmission. The simplicity of the actuation principle and the compatibility with micro system technologies make these materials very suitable for highly miniaturized and micro-electromechanical systems due to their simplicity of mechanism, high power/weight (or power/volume) ratios, and their clean, noiseless, spark-free, and frictionless operation.

During the lifespan of the SMA actuator, loss of actuation can occur through repeated cycling due to development of plastic strain. The characteristics associated with the transformation vary through cycle deformation, and fatigue occurs under deformation with high cycles. The important external parameters that affect the reliability of SMA actuators are time, temperature, stress, transformation strain, and the amount of transformation cycles. The important internal parameters that determine the physical and mechanical properties are the alloy composition, type of transformation and the lattice structure including defects. Any alteration in SMA actuation properties will necessarily affect the device into which it is incorporated, which may be critical in devices such as micro-actuators which are required to reliably function in a repeatable manner.

Thus, the behavior of the working characteristics when subjected to thermomechanical cycles becomes crucial in designing the SMA element. It is known that the behavior of the SMA material is a function of transformation temperature, stress, and strain. Based on a specific application, it is of great importance to measure these parameters in an SMA actuator of a particular configuration, to reliably predict the lifespan and reliability of the device incorporating it. It is also important to be able to reliably assess the thermomechanical properties of particular shape memory alloys having particular dimensions, to allow the design of SMA actuators with predictable mechanical properties.

SUMMARY OF THE INVENTION

In accordance with the purposes of the present invention as described herein, in one aspect the present invention provides an instrument for measuring a property of a shape memory alloy such as a thermomechanical property, comprising a base plate, a non-contact movable mass adapted for reversible linear displacement, a force gauge, an actuator for applying a preload force, a biasing spring, a heater for heating the shape memory alloy, and a non-contact displacement detector. The movable mass and force gauge may include first holders for holding the shape memory alloy therebetween. Similarly, the actuator and the movable mass may include second holders for holding the biasing spring therebetween.

The biasing spring and the shape memory alloy are disposed on opposed sides of the movable mass in such a fashion that a force applied to the movable mass thereby is applied substantially through a center of stiffness of the movable mass. This feature advantageously prevents movement of the movable mass which may increase roll, pitch, or yaw error rotations thereof The displacement detector preferably measures a displacement of the movable mass in a colinear direction with a direction of movement of the movable mass and with a direction of the force applied is by the biasing spring and the shape memory alloy. This results in minimizing Abbe error, further improving the accuracy and sensitivity of the device. The shape memory alloy (SMA) selected may be any substance having the desired properties of SMA as described above. Typically, the SMA will be in a wire form, but other shapes such as cables or ribbons are also anticipated. The actuator may be any actuator providing the desired sensitivity, such as a micrometer.

The non-contact movable mass comprises a linear motion stage supported by a non-contact bearing, and may include a housing and at least one guide bar. As will be described in greater detail below, typically the guide bar length and base plate length will be selected whereby a calculated axial expansion of the guide bar is substantially equal to a calculated axial expansion of the base plate. This minimizes the error in displacement or force measurements that would be introduced by different coefficients of thermal expansion and ambient temperature fluctuations.

The force gauge may be any detector of suitable sensitivity, such as a load cell. A current detector may also be provided for measuring a current applied to the SMA. Similarly, a voltage detector for measuring a voltage applied to the SMA may be provided. Additionally, a low thermal impedance temperature sensor with an electrically insulating layer can be attached to the SMA to provide temperature measurements during material transformation. Typically, a data acquisition system will be provided for acquiring and processing the current, force, voltage, and displacement data.

The displacement detector may be any detector of suitable sensitivity. In one embodiment of the invention, the displacement detector is a laser interferometer system. In another embodiment, the displacement detector is a non-contacting capacitive displacement sensor such as a linear variable differential transformer transducer.

In another aspect of the present invention, an instrument for measuring a property of a shape memory alloy is provided, comprising a base plate, a non-contact movable mass which comprises a linear motion stage supported by a non-contact bearing, a force gauge, an actuator for applying a preload force, a biasing spring, a heater for heating the shape memory alloy, and a non-contact displacement detector. The linear motion stage comprises a housing and at least one guide bar, wherein a calculated axial expansion of the guide bar is substantially equal to a calculated axial expansion of the base plate as described above.

The movable mass and force gauge typically include first holders is for holding the shape memory alloy therebetween, and the actuator and the movable mass include second holders for holding the biasing spring therebetween. The biasing spring and the shape memory alloy are thereby disposed on opposed sides of the movable mass. Typically, the biasing spring and the shape memory alloy are disposed whereby a force applied thereby is applied substantially through a center of stiffness of the movable mass as described. As described above, the displacement detector typically measures a displacement of the movable mass in a colinear direction with a direction of movement of the movable mass and with a direction of the force applied by the biasing spring and the extension and contraction of the shape memory alloy. Other features of the present invention are as described above.

In yet another aspect of the present invention, a method is provided for measuring a thermomechanical property of a shape memory alloy, comprising the steps of attaching the shape memory alloy at a first end to a force gauge and at a second end to a first side of a non-contact movable mass adapted for reversible linear displacement, substantially as described above. A biasing spring is attached at a first end to an actuator and at a second end to a second side of the non-contact movable mass which is opposite the first side. Next, the SMA is elongated to a predetermined length using the actuator.

Next, the SMA is heated to a first temperature, which as is known in the art will cause SMA to contract. Heating may be accomplished by any suitable means, such as resistive heating achieved by applying a predetermined current to the shape memory alloy for a predetermined time period. Heating may also be achieved by conductive heating, convective heating, radiation, and the like. A first displacement of the movable mass caused by the SMA contraction is then measured. Next, the SMA is cooled to a predetermined temperature, and a second displacement of the movable mass is measured. The second displacement is caused by a force exerted by the biasing spring as the SMA elongates to reassume its original length and shape.

As described above, the displacement detector measures a displacement of the movable mass in a colinear direction with a direction of movement of the movable mass and SMA with a direction of the force applied by the biasing spring and the shape memory alloy. Typically, the biasing spring and the shape memory alloy are attached to the movable mass whereby a force applied by the biasing spring and the shape memory is alloy is applied substantially through a center of stiffness of the movable mass.

The method of the invention further includes the steps of measuring a current applied to the shape memory alloy, measuring a voltage applied to the shape memory alloy, and measuring a force exerted by the shape memory alloy heated to the first temperature. Multiple cycles of heating and cooling may be applied to the SMA and quantitated as described above using a suitable data acquisition system. It will be appreciated by the skilled artisan that the method of the present invention therefore provides a means for accurately measuring and quantitating properties of SMA subjected to repetitive cycles of heating/contraction and cooling/elongation, such as thermomechanical properties. Using the method of the present invention, and the instruments thereof, it is possible to accurately characterize SMA cycle deformation and fatigue resulting from repeated contraction/elongation cycles. Performance over time of devices such as actuators utilizing SMA can thereby be optimized and predicted.

Other objects and applications of the present invention will become apparent to those skilled in this art from the following description wherein is there is shown and described a preferred embodiment of this invention, simply by way of illustration of the modes currently best suited to carry out the invention. As it will be realized, the invention is capable of other different embodiments and its several details are capable of modification in various, obvious aspects all without departing from the invention. Accordingly, the drawings and descriptions will be regarded as illustrative in nature and not as restrictive.

BRIEF DESCRIPTION OF THE DRAWING

The accompanying drawing incorporated in and forming a part of the specification illustrates several aspects of the present invention and, together with the description, serves to explain the principles of the invention. In the drawing.

Reference will now be made in detail to the presently preferred embodiments of the invention, examples of which are illustrated in the accompanying drawing.

DETAILED DESCRIPTION OF THE INVENTION

In accordance with the identified need in the art, the present invention provides an instrument and a method for characterizing a property of a SMA wire such as thermomechanical properties and the like. The instrument is robust, precise, and minimizes major sources of error in measurement.

EXAMPLE 1

Figure 1:
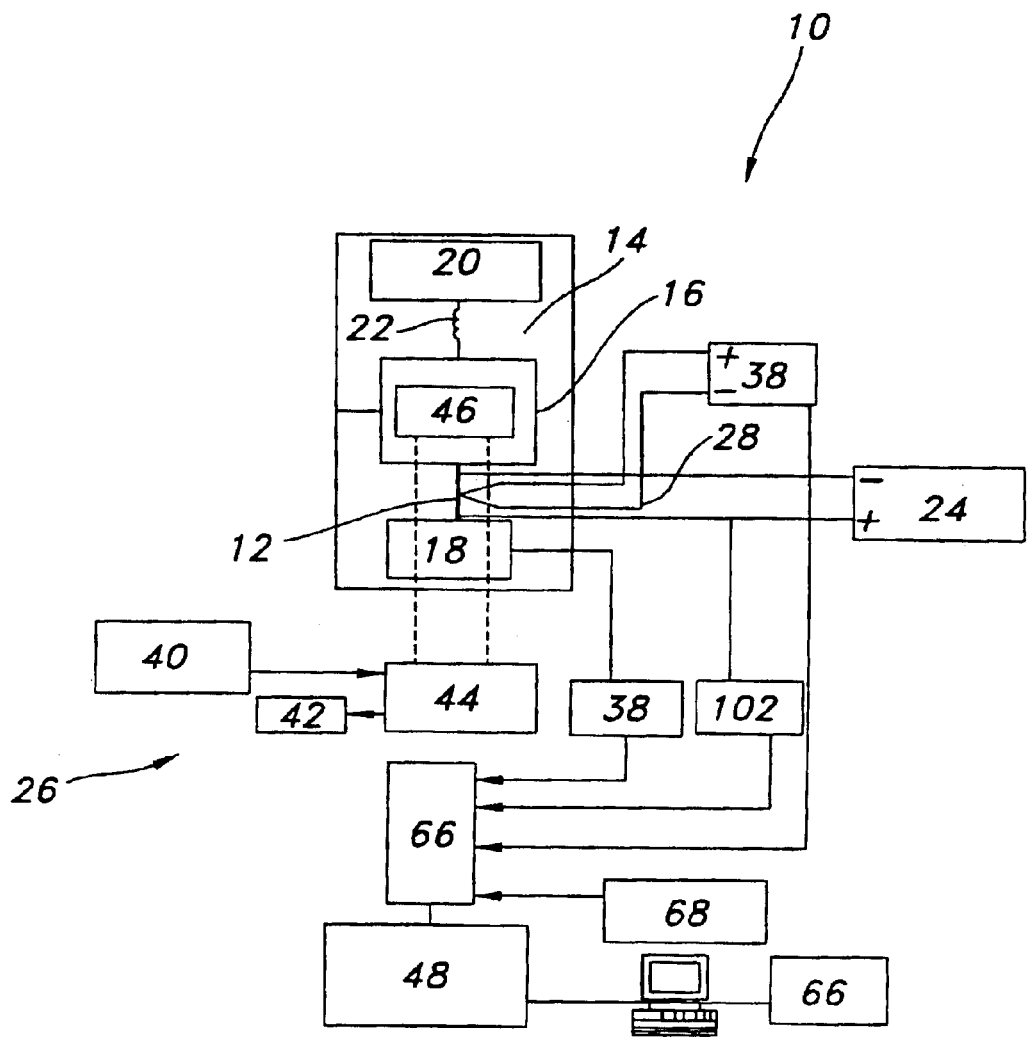
FIG. 1 schematically illustrates one embodiment of an instrument for characterizing a shape memory alloy in accordance with the present invention.

An instrument 10 for measuring a property of a shape memory alloy wire 12 is shown schematically in FIG. 1. The instrument 10 includes a base plate 14, a non-contact movable mass 16, a force gauge 18, an actuator 20, and a biasing spring 22 operatively connecting the movable mass 16 and the actuator 20. SMA wire 12 is attached between the movable mass 16 and the force gauge 18. Actuator 20 is a micrometer, and extending or retracting the micrometer adjusts the preload force on the SMA wire 12 via biasing spring 22. Force gauge 18 is a load cell capable of measuring the force generated by the SMA wire 12 during actuation. Actuation of the SMA wire 12 is initiated by supplying a voltage from s power supply 24. The current being supplied will vary on the diameter of the SMA wire 12 being tested. Required currents in accordance with various SMA wire diameters may be obtained from the manufacturers.

The position of the movable mass 16 caused by SMA wire 12 actuation is measured using a displacement detector 26 which will be described in greater detail below. The temperature of the SMA wire 12 during actuation is measured by a thermocouple 28.

Figure 2:
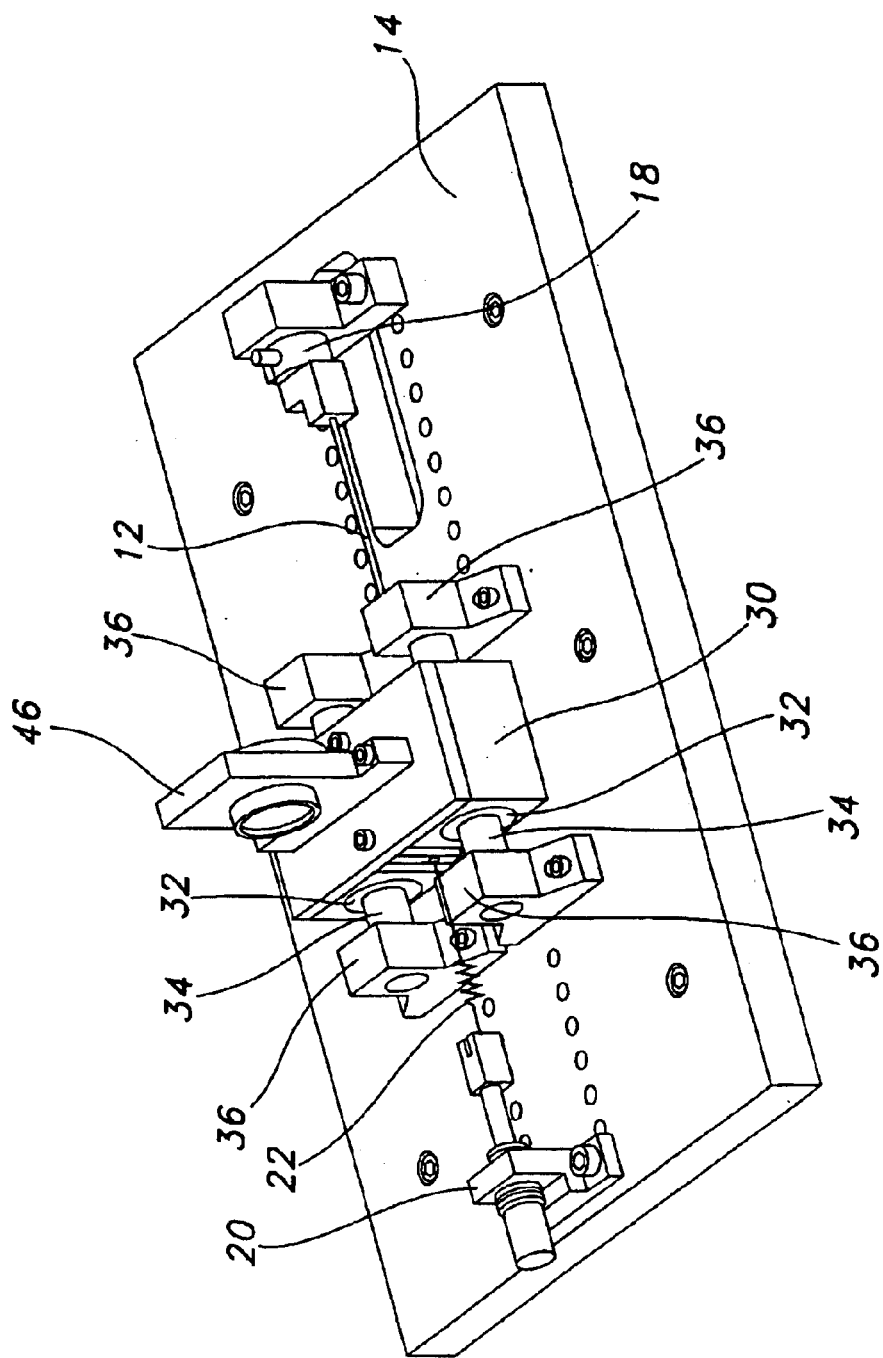
FIG. 2 illustrates a shape memory alloy wire attached to the instrument of FIG. 1.

FIG. 2 shows the movable mass 16 in greater detail. Movable mass 16 consists of a linear motion stage 30 supported on two cylindrical porous graphite air bearings 32 (Model No: S300601, New Way Machine components). The porous graphite cylindrical bearings 32 travel on stainless steel shafts 34. End mounts 36 fastened to the base plate 14 support this assembly. The important advantage offered by non-contact bearings 32 are low static and dynamic friction. This is important since friction force will introduce significant uncertainty in force and displacement measurement, as well as wear of components. The instrument 10 may be mounted on an optical table (not shown) to minimize the effects of vibration, improve the leveling of the linear motion stage 30, and minimize gravity loads on the wire 12.

An inline amplifier 38 may be included for signal amplification and conditioning (FIG. 1). In use, the test specimen is actuated by passing an electric current therethrough from power supply 24, causing it to contract. The temperature change of the SMA wire 12 due to resistive heating is measured by thermocouple 28. Displacement of movable mass 16 is measured using a laser interferometer system (see FIG. 3).

Figure 3:
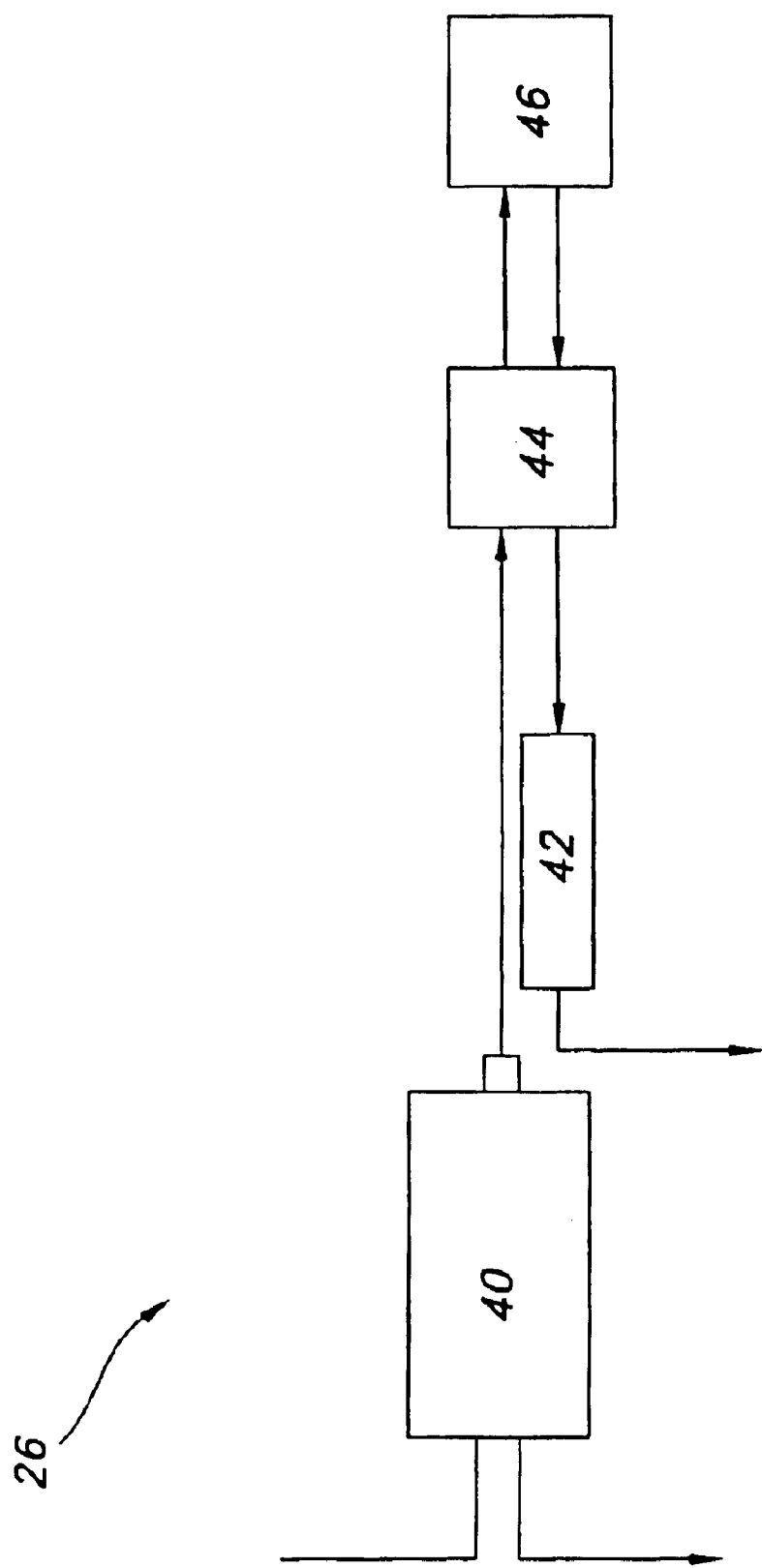
FIG. 3 schematically illustrates the displacement detector of the instrument of FIG. 1.

Referring to FIG. 3, a displacement detector 26, consisting of a laser interferometer system is shown schematically. The system includes a laser head 40 which is the reference for all measurements of the system, a receiver 42 which detects displacement of either an interferometer 44 or a retroreflector 40 and generates a measurable signal. As shown in FIG. 2, the retroreflector 46 may be carried on the linear motion stage 30. The reference and measurement signals are compared by methods known in the art to generate displacement information. Accordingly, movement of the movable mass 16 may be detected and quantitated.

Figure 4:
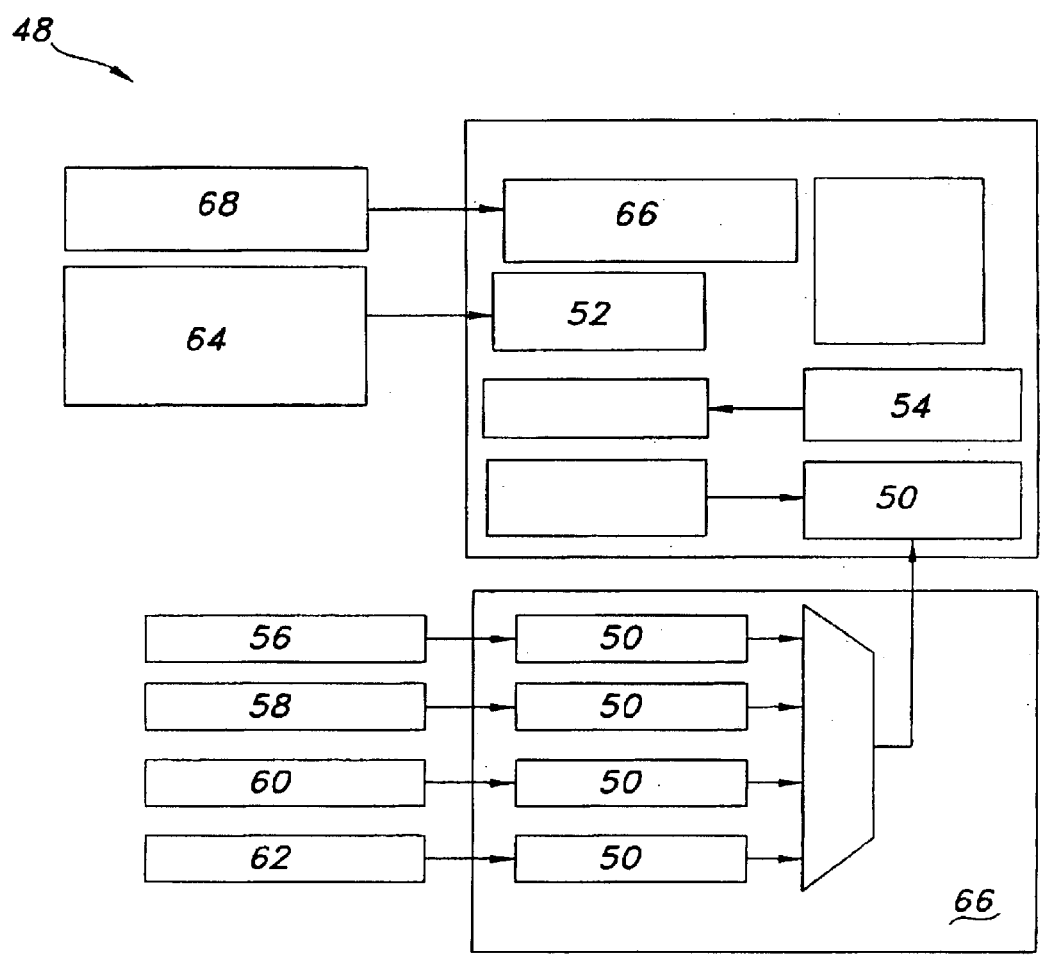
FIG. 4 schematically illustrates the data acquisition system of the instrument of FIG. 1.

The present invention includes a data acquisition system 48, shown schematically in FIG. 4, for collecting and processing current, force, voltage, and displacement data. In the present embodiment of the instrument, the data acquisition system 48 was a 16-Bit, 200 kHz Analog to Digital (A/D) Converter with 16-Bit Digital to Analog (D/A) converters 80 and Digital I/O lines 52 (PCI DAQBOARD-2001, Iotech, Inc., hosted in a personal computer). The data acquisition system 48 used four A/D converters 54 for acquiring data such as current 56 across the SMA wire 12, voltage 58 across the SMA wire 12, force measurements 60, temperature measurements 62 and one D/A converter 50 for capturing the displacement measurement from the 16-Bit up/down counter 64. A 4-channel simultaneous sample and hold card 66 was used to enable the samples of current 56, voltage 58, temperature 62 and force 60 to be taken at the same instance in time and then multiplexed to the main ADC for digitalization. The DAQBOARD was triggered by an external TTL pulse 66 provided by an experiment control unit 68. On triggering, the data acquisition system 48 sampled and stored simultaneously measured four analog inputs, namely, the current reading, voltage reading, force reading and temperature reading. In addition, the system stored the count that indicates the position of the movable mass 16 as measured by the laser interferometer.

An experiment controller 68 (Microchip PIC16F84 8-bit flash-chip in an 18-pin DIP package) was included for simpler prototyping. The controller features 1K-program flash, 132 byte Data RAM, and runs at a maximal clock frequency of 10 MHz. The experiment controller 68 communicates with the RS-232 serial port of a generic PC. The software allowed the user to input the experimental parameters after the timer and port initializations. The parameters input were number of desired actuation cycles, amount of current that needs to be passed through the SMA wire (per the manufacturers directions), amount of time the current has to be passed through the SMA wire (per the manufacturers directions), and cooling time.

The voltage and current consumed by the wire sample during each actuation cycle was measured to monitor the fluctuation in these values over a number of actuation cycles. The voltage across the sample wire was measured by a high-resistance ($5 \times 10^{12}$ $\Omega$) analog input of the 4-channel sample and hold card 66. The current across the wire was measured using a mA-2000™ current meter (F.W. Bell Technologies). The output of the current meter was recorded by connecting the analog output, (1 mV/mA) of the current meter to the analog input channel of the data acquisition system.

EXAMPLE 2

FLEXINOL wire having a diameter of 38.1 $\mu$m, 50.8 $\mu$m, 101.6 $\mu$m, and 152.4 $\mu$m (Dynalloy Inc, Costa Mesa, Calif.) was tested using the instrument described in Example 1. The material composition is 55.3% Ni by weight, Ti (Balance) and impurities less than 0.03%. The actuation temperatures of the material under 100 MPa load are recovery/contraction temperature of 70° C. ±15° C. and extension/cooling temperature of 50° C. ±15° C.

A pre-crimped SMA wire 12 was attached between the force gauge 18 and one end of the linear motion stage 30 using non-metallic screws and washers. A biasing spring 22 was connected between the other end of the linear motion stage 30 and the actuator 20. The preload force was calculated based on the preload stress in the wire (Table 1).

TABLE 1

| Preload and Actuation Stress | |
| --- | --- |
| Actuation stress, Pa | $1 \times 10^8$ |
| Preload stress, Pa | $7 \times 10^7$ |

Nominal preload forces for different wire 12 diameters are provided in Table 2.

TABLE 2

Preload Forces for Different Wire Diameters

| Diameter of Wire ($\mu$m) | Cross-sectional Area (m$^2$) | Preload Force (N) |
|---|---|---|
| 38.1 | 1.140 × 10$^{-9}$ | 0.0798 |
| 50.8 | 2.026 × 10$^{-9}$ | 0.1418 |
| 101.6 | 8.107 × 10$^{-9}$ | 0.5674 |
| 152.4 | 1.824 × 10$^{-8}$ | 1.2768 |

The current and voltage to achieve a desired actuation of SMA wire 12 was obtained from the manufacturer's specification. The corresponding force and displacement for each actuation cycle is recorded by the data acquisition system.

Figure 5A:
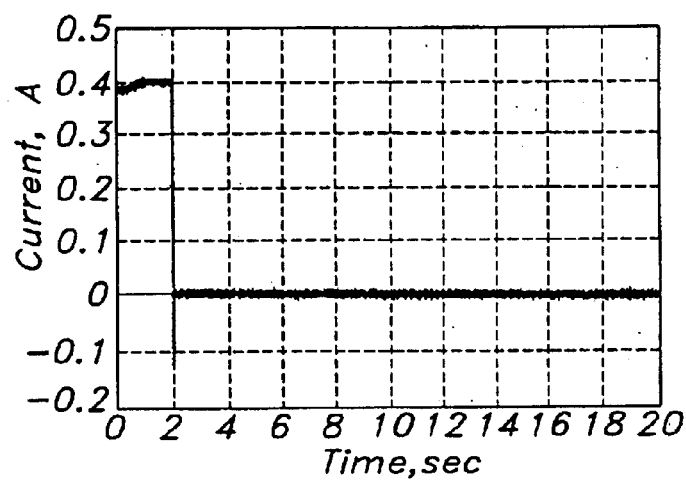
FIGS. 5*a*–5*c* are plots of measured characteristics of shape memory alloy wire obtained using the instrument of FIG. 1: (*a*) current characteristics for a 152.4 $\mu$m×0.0508 m FLEXINOL wire; (b) voltage characteristics for a 152.4 $\mu$m×0.0508 m FLEXINOL wire; (c) resistance change characteristics for a 152.4 $\mu$m×0.0508 m FLEXINOL wire.
Figure 5B:
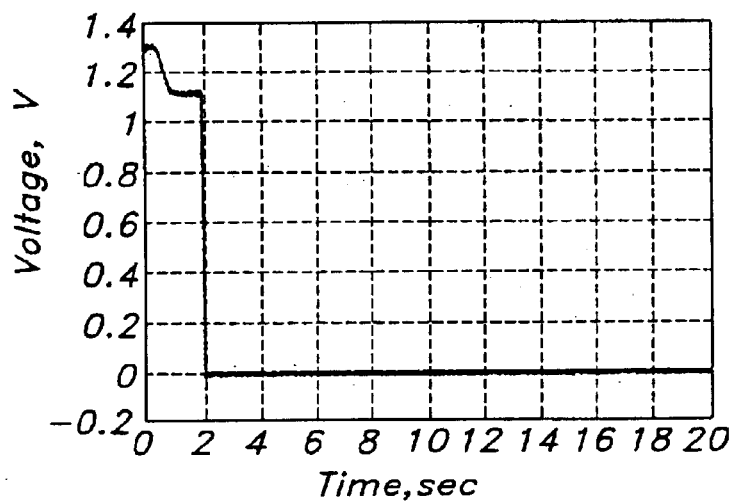
Figure 5C:
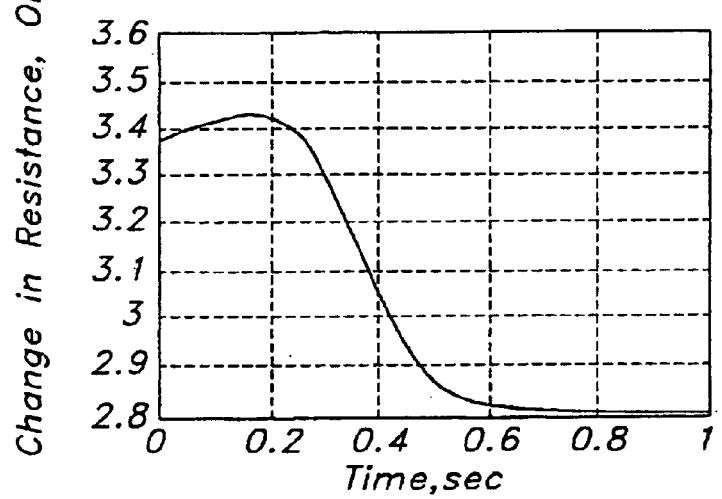

FIG. 5a illustrates the current characteristics for a 152.4 $\mu$m×0.0381 m FLEXINOL wire. FIG. 5b shows the voltage curve for the wire. FIG. 5c shows the change in the resistance of the wire during the actuation cycle, calculated by the ratio of voltage change across the wire and the current supplied to the wire. Based on the diameter of the wire, 400 mA of current (based on the manufacturer's specification) was supplied. The current was initially zero and was rapidly increased to the maximum value. This amount of current was maintained for a period of two seconds during which the actuation took place.

Figure 6:
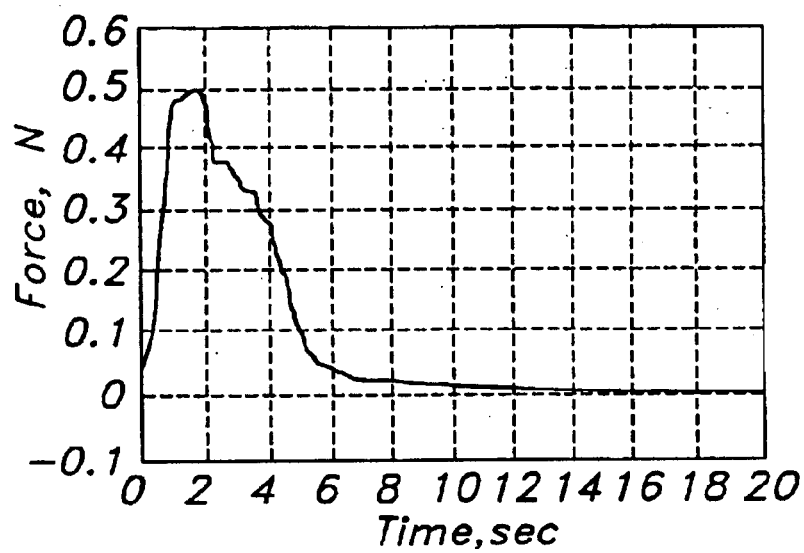
FIG. 6 is a plot of filtered force characteristics for a characteristics for a 152.4 $\mu$m×0.0508 m FLEXINOL wire.

FIG. 6 illustrates the transient force characteristics for a 152.4 $\mu$m×0.0508 m SMA wire. The force on the wire was initially due to the preload force established by the tension spring. A ringing in the force curve (not shown) was observed which was believed to be a result of the transient state of the wire, which results in the vibration of the movable mass. The force in the wire became steady after the initial ringing, and began to decrease as soon as the current to the wire was discontinued. The force exerted by the SMA wire was calculated using Equation (1).

$$\text{Force (N)} = (\text{Voltage Reading}/5) \times 9.81 \quad (1)$$

A low pass filter was used to eliminate noise in the force measurements. The filtered data (FIG. 6) was used for calculating the actuation stress in the wire for plotting the stress-strain diagrams for the particular diameter wire.

Figure 7:
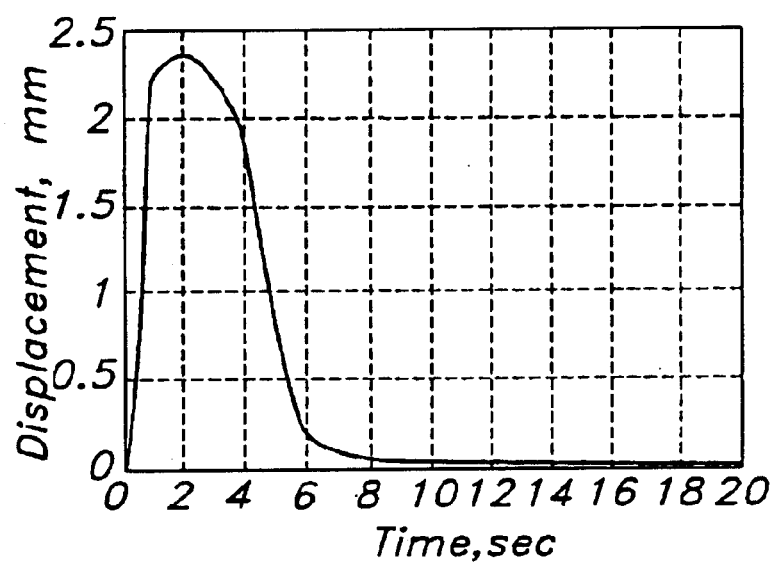
FIG. 7 is a plot of displacement characteristics for a 152.4 $\mu$m×0.0508 m FLEXINOL wire.

FIG. 7 illustrates a representative displacement curve for a 152.4 $\mu$m×0.0508 m SMA wire. Actuation of the SMA wire was directly proportional to the movement of the movable mass 16. The movable mass 16 moved as the wire contracted in response to resistive heating, and returned to its initial position as the wire cooled. The displacement of the mass was measured using Equation (2)

$$\text{Displacement(mm)} = \text{Counts} \times 6.23 \times 10^{-6}/25.4 \quad (2)$$

where 6.23×10$^{-6}$ was the wavelength of the laser beam used.

Figure 8:
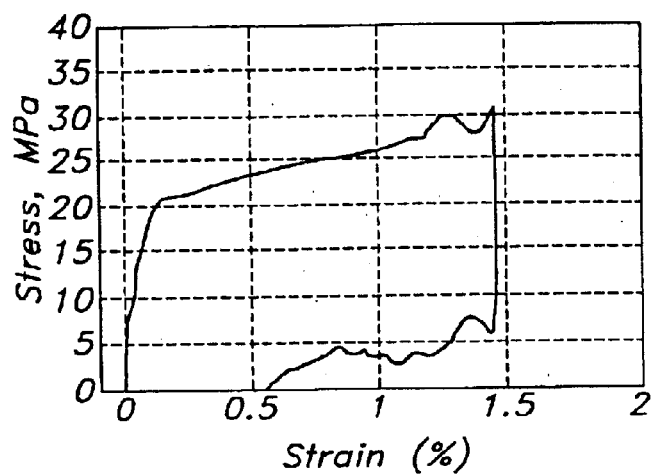
FIG. 8 is a plot of a stress-strain curve for a 152.4 $\mu$m×0.0254 m FLEXINOL wire.

FIG. 8 illustrates a stress-strain curve for a 152.4 $\mu$m×0.0254 m wire, showing the shape memory effect—a "dynamic" stress-strain curve derived from the transient force and displacement curves. Here, a full is shape recovery was observed because of heating the SMA material above the austenite start temperature. This curve was not a statically determined stress-strain curve such as one might measure on a tensile screw machine. These results illustrate a complete pseudoelastic effect where unloading of the SMA results in total reversion to its initial position after going through a mechanical hysteresis.

EXAMPLE 3

Figure 9A:
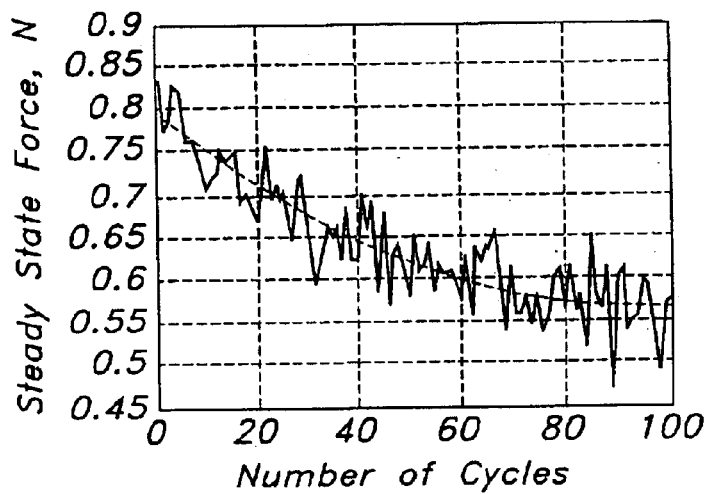
FIGS. 9*a*–9*b* plot the variation over 100 actuation cycles in force (N) (FIG. 9*a*) and in displacement (mm) (FIG. 9*b*) for a 152.4 $\mu$m33 0.0508 m FLEXINOL wire.
Figure 9B:
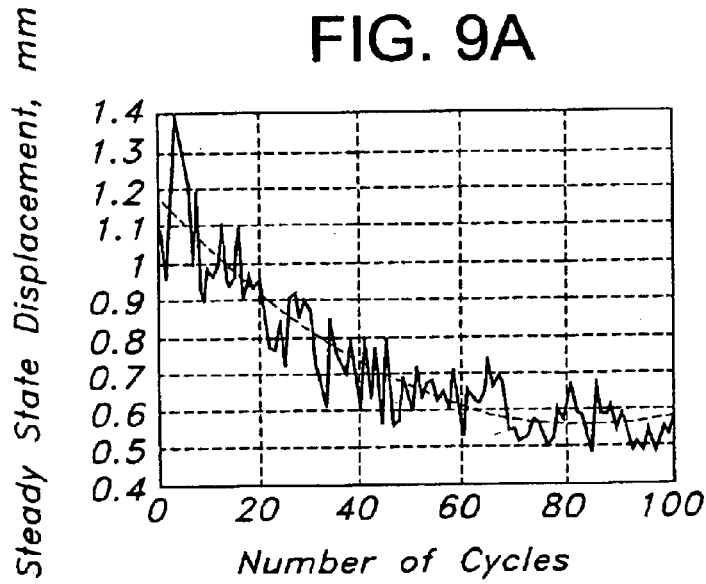

The instrument 10 described in Example 1 was used to evaluate the effect of multiple actuation cycles of a SMA wire 12. The wire 12 was attached to the instrument as described in Examples 1 and 2. Desired voltage, current, number of actuation cycles, time of supply of current, and cooling time were input using controller 68. Variation in force and displacement were recorded by the data acquisition system 48, using the calculations described in Example 2. As shown in FIGS. 9a and 9b, the instrument recorded the variation in steady state force and displacement over 100 actuation cycles. It was shown that steady state force and displacement decrease with increasing number of actuation cycles, illustrating mechanical fatigue of the SMA wire 12 over time.

EXAMPLE 4

Figure 10:
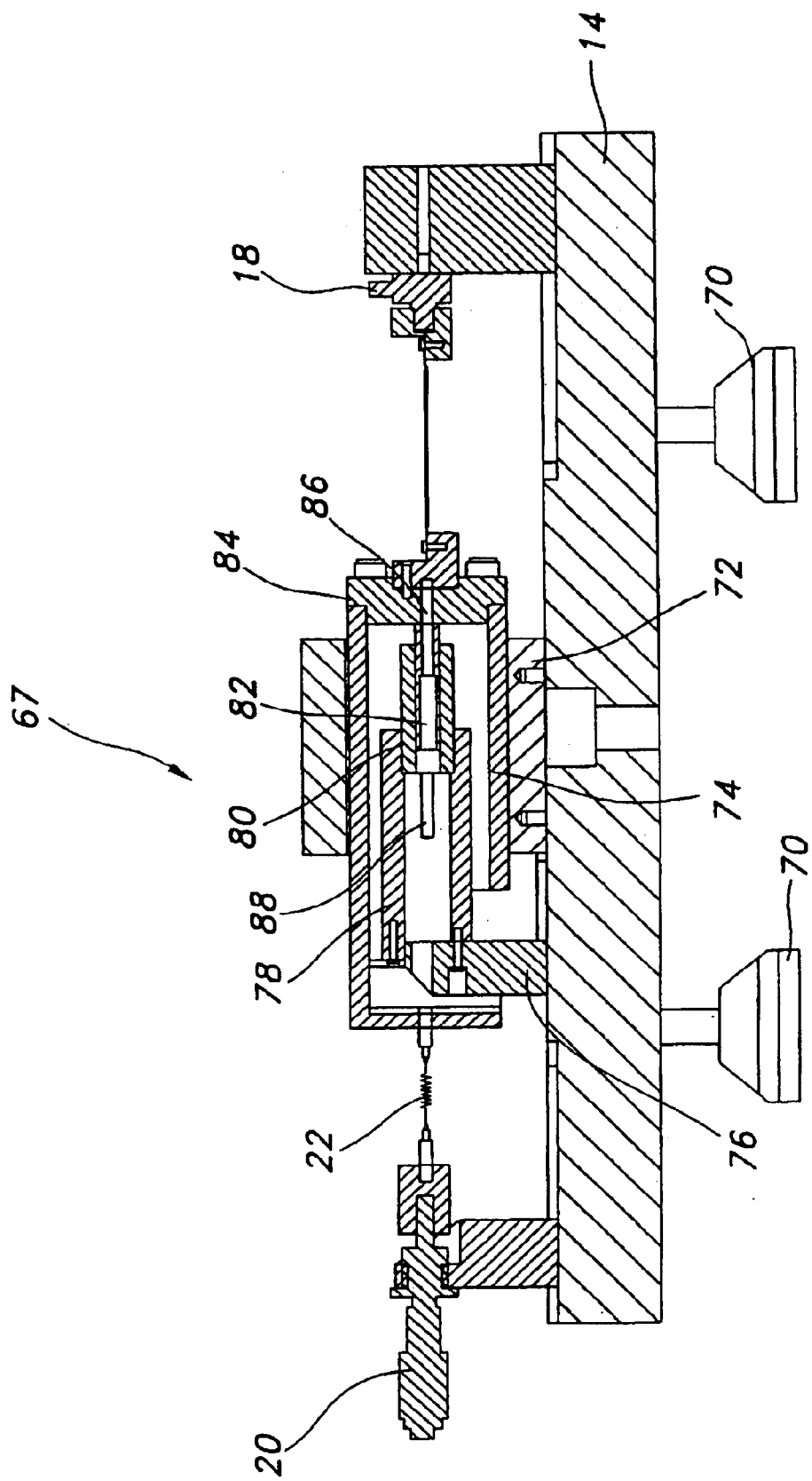
FIG. 10 schematically illustrates another embodiment of the instrument of the present invention.

A second embodiment of the instrument, labeled with reference numeral 67, of the present invention is shown schematically in FIG. 10. The actuator 20, biasing spring 22, and force gauge 18 are substantially as described in Example 1. Base plate 14 is fabricated of a material designed to maximize the structure's stiffness to weight ratio. In the embodiment depicted in FIG. 10, the base plate may be machined from cast iron (CI-30). Vibration isolating legs 70 reduce vibration of base plate 14 without requiring an optical table or other device as in the instrument of Example 1. Movable mass 16 consists of a linear motion stage supported by an air bearing. As shown in FIG. 10, in this embodiment the air bearing consists of a linear motion stage supported by a porous graphite air bearing consisting of a housing 72 and an aluminum guide bar 74.

Figure 11:
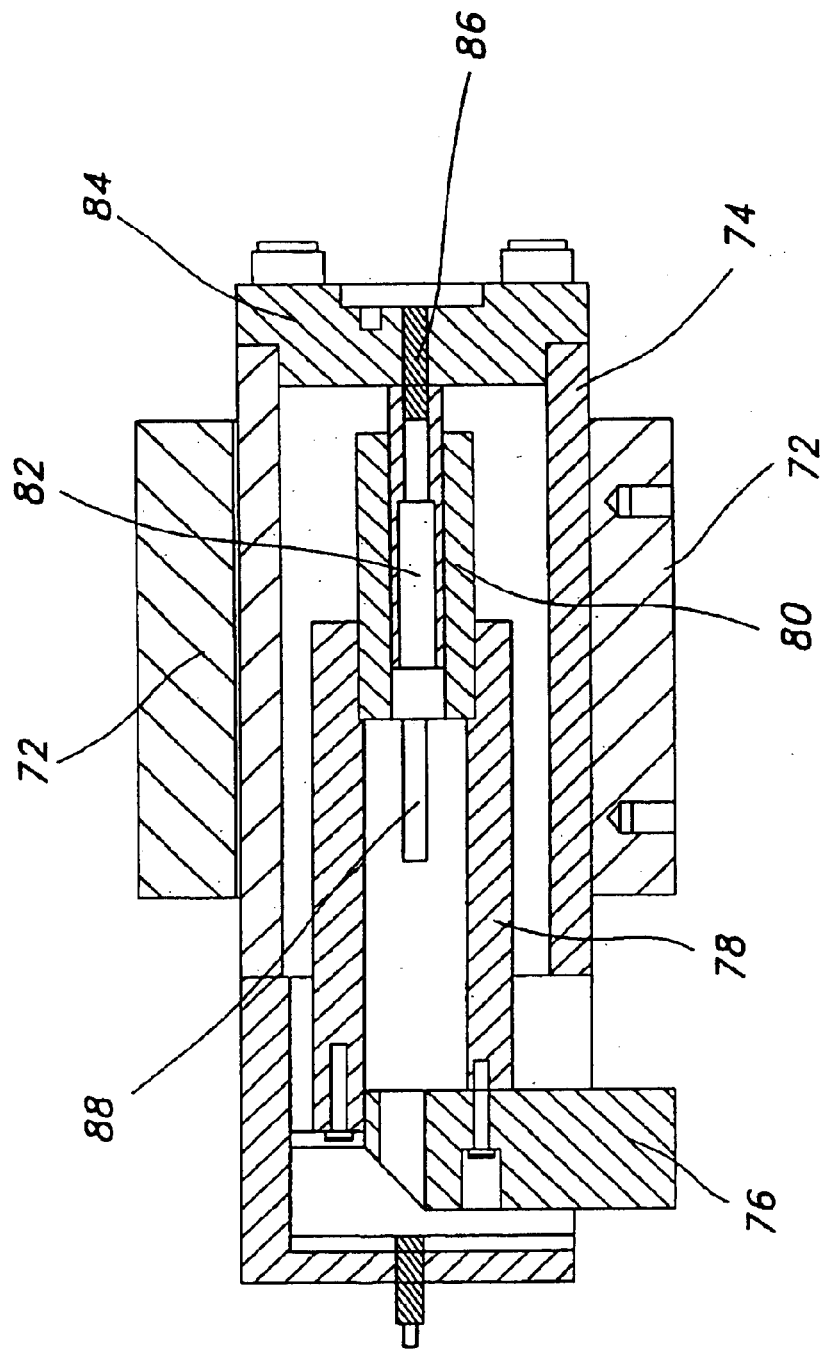
FIG. 11 shows the displacement detector of the instrument of FIG. 10 in greater detail.

The displacement detector 26 comprises an LVDT transducer carried within the guide bar 74 as shown in FIG. 11. A clamp holder 76 is and clamp 78 hold LVDT transducer 80 in place. LVDT core 82 is mounted to an end plate 84 on guide bar 74 by threaded stud 86. Lead 88 transmits displacement data from LVDT core 82 to the data acquisition system.

Figure 12:
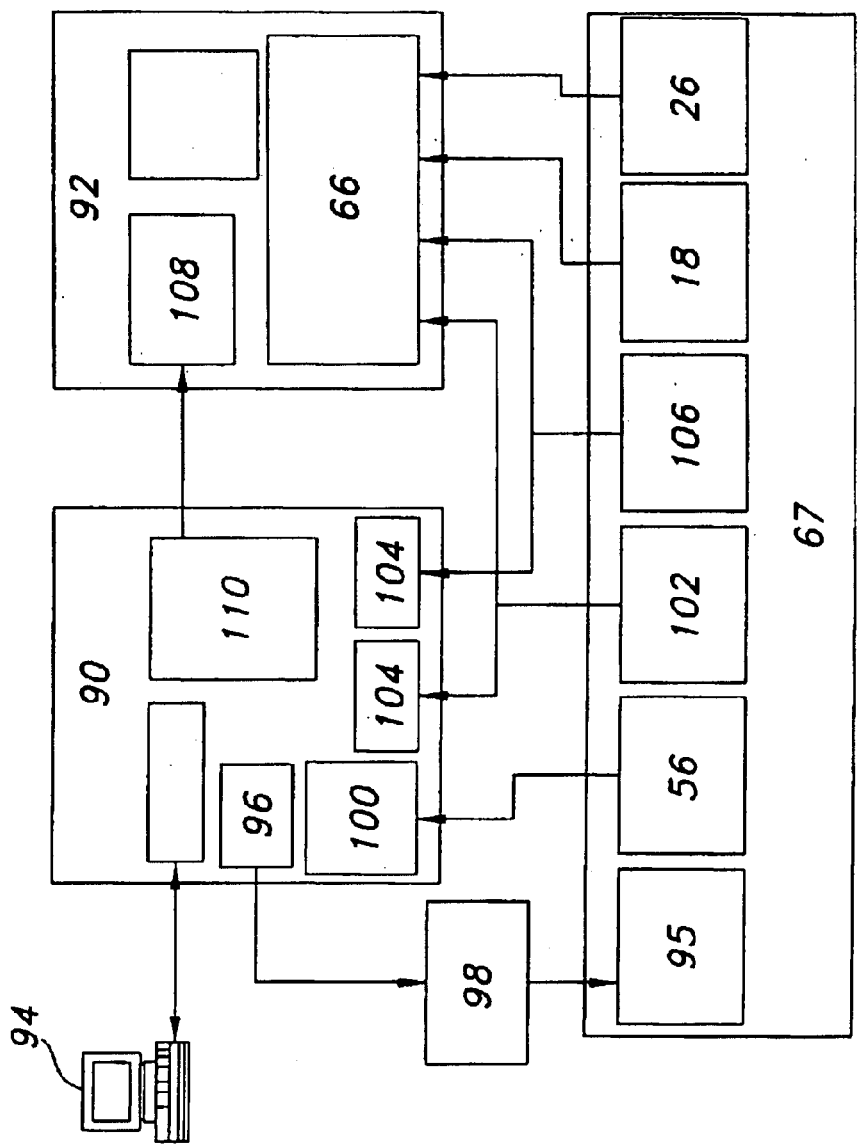
FIG. 12 schematically shows the controller and data acquisition system of the instrument of FIG. 10.

The instrument 67 includes a controller 90 and data acquisition system 92, represented schematically in FIG. 12, which comprises four major components. First is the instrument 67 (not shown in this view). The data acquisition system 92 collects data and stores it on a personal computer 94 hosting it. A user interface is provided which allows the setting of experimental parameters. Finally, a microcontroller-based control circuit 95 is provided to execute the experiments using power and temperature feedback loops, using the predetermined experimental parameters input by the user.

The SMA wire 12 being tested is driven by the microcontroller 95 using a 10 V digital to analog converter (DAC) 96 and amplified by an operational amplifier (OPAMP) 98, which excites the gate of a MOSFET switching transistor. Voltage drop across the wire 12 is measured by two analog inputs 100 of the microcontroller 95 operating in differential mode. Actual current passing through the wire 12 is measured using a non-contact current meter 102. The meter 102 outputs an analog voltage, which is connected to an analog input on the DAQ system 92 and to an analog to digital converter (ADC) 104 on the microcontroller 95. The temperature of the sample is measured using a temperature sensor 106 such as a thermocouple. The linear output of the temperature sensor 106 is recorded through an input on the DAQ system 92 and monitored by the microcontroller's ADC 104 subsystem. Similarly, the output of the load cell 18 and the analog output of the displacement detector 26 is connected to the DAQ system 92 and the controller 90. The DAQ system 92 is triggered by an external TTL trigger 108 from a general purpose input output pin (GPIO) 110 on the controller 90 to record the four desired analog sensor values (current, temperature, force, and displacement).

The experimental parameters are set by the user through standard serial terminal software running on a host PC 94 and communicating with the microcontroller 95 in RS232. The number of actuations, duration, and cooling time between each two-actuation cycles can be set. In addition, the amount of current, target temperature, or voltage drop across the sample wire can be set. The microcontroller 95 uses the feedback information to adjust the actuation power by varying the state of the MOSFET switch In addition, the user can enter pairs of time and target values allowing the sample to be driven with custom voltage, current, or temperature profiles. This embodiment of the instrument enables a wide variety of testing scenarios. For example, the statistical distribution of SMA wire performance parameters may be studied by conducting repetitive identical actuations. Force exertion may be studied as a function of power or temperature. In addition, the effect of different powering techniques such as DC, PWM, or high current bursts may be investigated.

Thermal effects contribute significantly to the uncertainty of precision machines and instruments. Temperature gradients in the instrument parts such as the guide bar 74 can cause angular errors, which lead to Abbe errors in displacement measurement Such errors are minimized in the present instrument 67 by matching the axial expansion of the guide bar 74 with that of the base plate 14.

The axial expansion of the base plate 14 material, $\delta_{BP}$, with a coefficient of thermal expansion, $\alpha_{BP}$, length, $L_{BP}$, and a temperature fluctuation of $\Delta T$, is expressed by Equation (3).

$$\delta_{GB} = \alpha GB L_{GB} \Delta T \tag{3}$$

Similarly, the axial expansion of the guide bar 74 material, $\delta_{GB}$, with a coefficient of thermal expansion, $\alpha_{GB}$, length $L_{GB}$, and a temperature fluctuation of $\Delta T$, is given by Equation (4).

$$\delta_{GB} = \alpha_{GB} L_{GB} \Delta T \tag{4}$$

Since the lengths of the SMA wire, $L_W$ and the tension spring, $L_S$, should be constant, the uncertainty in force measurement, $U_F$ that results from thermal expansion is a function of stiffness of the spring, $k_s$, $\alpha_{BP}$, $L_{BP}$, $\alpha_{GB}$, $L_{GB}$, $\Delta T$ and is expressed as shown in Equation (5).

$$U_F = k_S \Delta T (\alpha_{BP} L_{BP} - \alpha_{GB} L_{GB}) \tag{5}$$

The uncertainty in the displacement measurement, $U_D$ is a function of temperature, $\Delta T$, length of the base plate, $L_{BP}$, and length of guide bar, $L_{GB}$ and is given by Equation (6).

$$U_D = \Delta T (\alpha_{BP} L_{BP} - \alpha_{GB} L_{GB}) \tag{6}$$

To minimize the uncertainty in the force and displacement measurement, the parenthesis term in the above two equations should be equal to zero. Therefore, the ratio of coefficient of thermal expansion (CTE) should be equal to the ratio of lengths. In the instrument 67 embodiment depicted in Example 4, the guide bar 74 may be fabricated of aluminum, (Al-6061 with, $\alpha=23.0\times10^{-6}1/°$ C.) and the base plate may be fabricated of Cast Iron (CI-30 with $\alpha=10.0\times 10^{-6}1/°$ C.) and the appropriate base plate 14 length to minimize $U_F$ is 400.0 mm.

Figure 13:
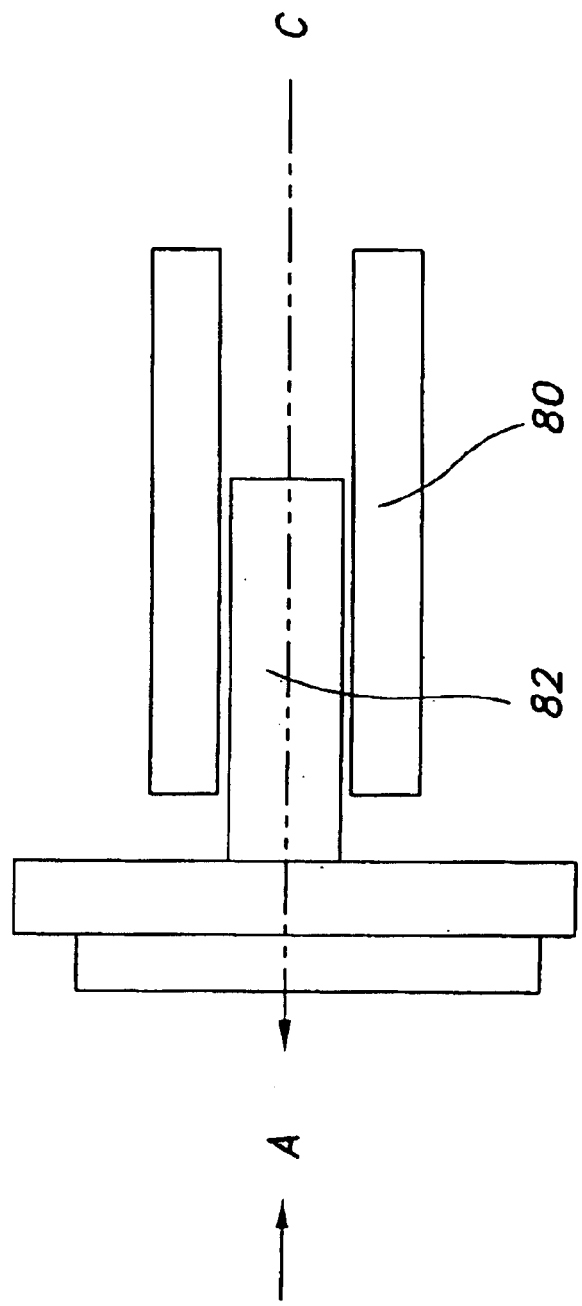
FIG. 13 shows the configuration of the displacement detector for minimizing Abbe error.

Advantageously, the displacement detector 26 of the instrument 67 measures displacement of the movable mass 16 in a collinear direction with a direction of movement of the movable mass, and with a direction of the force applied by the biasing spring 22 and the SMA wire 12. Bryan's principle states: "The displacement measuring system should be inline with the functional point whose displacement is measured. If this is not possible, either the slideways that transfer the displacement must be free of angular motions or angular motion data must be used to calculate the consequences of the offset". In the instrument of the present invention, such error is minimized. Further, placing the displacement detector 26 coaxially with a center of stiffness C of the air bearing and the line of actuation A along which displacement is measured (see FIG. 13) also results in minimizing error.

Accordingly, a robust and precise instrument for characterizing thermomechanical properties of a shape memory alloy is provided, along with methods for characterizing such thermomechanical properties. The instrument minimizes major sources of error in measurement. The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

What is claimed is:

1. An instrument for measuring a property of a shape memory alloy, comprising:
    a base plate;
    a non-contact movable mass adapted for reversible linear displacement;
    a force gauge;
    an actuator for applying a preload force;
    a biasing spring;
    a heater for heating the shape memory alloy; and
    a non-contact displacement detector;
    wherein the movable mass and force gauge include first holders for holding the shape memory alloy therebetween, and the actuator and the movable mass include second holders for holding the biasing spring therebetween, whereby the biasing spring and the shape memory alloy are disposed on opposed sides of the movable mass.

2. The instrument of claim 1, wherein the biasing spring and the shape memory alloy are disposed whereby a force applied thereby is applied substantially through a center of stiffness of the movable mass.

3. The instrument of claim 2, wherein the displacement detector measures a displacement of the movable mass in a colinear direction with a direction of movement of the movable mass and with a direction of the force applied by the biasing spring and the shape memory alloy.

4. The instrument of claim 1, wherein the shape memory alloy is a shape memory alloy wire.

5. The instrument of claim 1, wherein the actuator is a micrometer.

6. The instrument of claim 1, wherein the movable mass comprises a linear motion stage supported by a non-contact bearing.

7. The instrument of claim 6, wherein the linear motion stage comprises a housing and at least one guide bar, and further wherein a calculated axial expansion of the guide bar is substantially equal to a calculated axial expansion of the base plate.

8. The instrument of claim 1, wherein the force gauge is a load cell.

9. The instrument of claim 1, further including a current detector for measuring a current applied to the shape memory alloy.

10. The instrument of claim 1, further including a voltage detector for measuring a voltage applied to the shape memory alloy.

11. The instrument of claim 1, further including a data acquisition system for acquiring and processing said current, force, voltage, and displacement data.

12. The instrument of claim 3, wherein the displacement detector is a laser interferometer system.

13. The instrument of claim 3, wherein the displacement detector is a capacitive displacement sensor.

14. An instrument for measuring a property of a shape memory alloy, comprising:
- a base plate;
- a non-contact movable mass, said movable mass comprising a linear motion stage supported by a non-contact bearing;
- a force gauge;
- an actuator for applying a preload force;
- a biasing spring;
- a heater for heating the shape memory alloy; and
- a non-contact displacement detector,
- wherein the linear motion stage comprises a housing and at least one guide bar, and further wherein a calculated axial expansion of the guide bar is substantially equal to a calculated axial expansion of the base plate.

15. The instrument of claim 14, wherein the movable mass and force gauge include first holders for holding the shape memory alloy therebetween, and the actuator and the movable mass include second holders for holding the biasing spring therebetween, whereby the biasing spring and the shape memory alloy are disposed on opposed sides of the movable mass.

16. The instrument of claim 14, wherein the biasing spring and the shape memory alloy are disposed whereby a force applied thereby is applied substantially through a center of stiffness of the bearings supporting the movable mass.

17. The instrument of claim 16, wherein the displacement detector measures a displacement of the movable mass in a colinear direction with a direction of movement of the movable mass and with a direction of the force applied by the biasing spring and the shape memory alloy.

18. The instrument of claim 14, wherein the shape memory alloy is a shape memory alloy wire.

19. The instrument of claim 14, wherein the actuator is a micrometer.

20. The instrument of claim 14, wherein the force gauge is a load cell.

21. The instrument of claim 14, further including a current detector for measuring a current applied to the shape memory alloy.

22. The instrument of claim 14, further including a voltage detector for measuring a voltage applied to the shape memory alloy.

23. The instrument of claim 14, further including a data acquisition system for acquiring and processing said current, force, voltage, and displacement data.

24. The instrument of claim 17, wherein the displacement detector is a laser interferometer system.

25. The instrument of claim 17, wherein the displacement detector is a linear variable differential transformer transducer.

26. A method for repetitive measuring of a thermomechanical property of a shape memory alloy wire, using the instrument of claim 14.

27. A method for measuring a thermomechanical property of a shape memory alloy, comprising the steps of:
(a) attaching the shape memory alloy at a first end to a force gauge and at a second end to a first side of a non-contact movable mass adapted for reversible linear displacement;
(b) attaching a biasing spring at a first end to an actuator and at a second end to a second side of the non-contact movable mass which is opposite the first side;
(c) elongating the shape memory alloy to a predetermined length using the actuator;
(d) heating the shape memory alloy to a first temperature;
(e) measuring a first displacement of the movable mass with a non-contact displacement detector;
(f) cooling the shape memory alloy to a second temperature; and
(g) measuring a second displacement of the movable mass with the displacement detector;
wherein the displacement detector measures a displacement of the movable mass in a colinear direction with a direction of movement of the movable mass and with a direction of the force applied by the biasing spring and the shape memory alloy; and wherein the biasing spring and the shape memory alloy are attached to the movable mass whereby a force applied by the biasing spring and the shape memory alloy is applied substantially through a center of stiffness of the movable mass.

28. The method of claim 27, wherein the shape memory alloy is heated by applying a predetermined current to the shape memory alloy for a predetermined time period.

29. The method of claim 27, wherein the non-contact movable mass comprises a linear motion stage supported by a non-contact bearing.

30. The method of claim 29, wherein the linear motion stage comprises a housing and at least one guide bar, and further wherein a calculated axial expansion of the guide bar is substantially equal to a calculated axial expansion of the base plate.

31. The method of claim 27, wherein the shape memory alloy is a shape memory alloy wire.

32. The method of claim 27, further including the steps of:
measuring a current applied to the shape memory alloy;
measuring a voltage applied to the shape memory alloy; and
measuring a force exerted by the shape memory alloy heated to the first temperature.

33. The method of claim 32, further including the step of subjecting the shape memory alloy to a predetermined number of heating and cooling steps.

* * * * *